United States Patent
Kawaguchi et al.

(10) Patent No.: US 9,513,236 B2
(45) Date of Patent: Dec. 6, 2016

(54) RADIATION DETECTING APPARATUS AND RADIATION TOMOGRAPHIC IMAGING APPARATUS

(71) Applicant: GENERAL ELECTRIC COMPANY, Schenectady, NY (US)

(72) Inventors: Kotatsu Kawaguchi, Tokyo (JP); Joseph James Lacey, Waukesha, WI (US); Richard Paul Vandeweghe, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 134 days.

(21) Appl. No.: 14/554,117

(22) Filed: Nov. 26, 2014

(65) Prior Publication Data

US 2015/0156920 A1    Jun. 4, 2015

Related U.S. Application Data

(60) Provisional application No. 61/910,184, filed on Nov. 29, 2013.

(51) Int. Cl.
  *A61B 6/03* (2006.01)
  *G01N 23/04* (2006.01)
  *A61B 6/00* (2006.01)

(52) U.S. Cl.
  CPC ............. *G01N 23/046* (2013.01); *A61B 6/032* (2013.01); *A61B 6/4488* (2013.01)

(58) Field of Classification Search
  CPC .. G01N 23/046; A61B 6/032; A61B 6/4488; G01T 1/20; H05K 7/20145; H05K 7/20163
  See application file for complete search history.

(56) References Cited

U.S. PATENT DOCUMENTS

| | | | |
|---|---|---|---|
| 6,330,153 B1 * | 12/2001 | Ketonen | H05K 7/20145 165/104.33 |
| 6,490,871 B1 | 12/2002 | Stautner | |
| 7,112,966 B2 | 9/2006 | Motoshiromizu et al. | |
| 7,499,525 B2 | 3/2009 | Horndler et al. | |
| 8,890,079 B2 | 11/2014 | Kurochi et al. | |
| 8,890,080 B2 | 11/2014 | Kuroda et al. | |
| 2007/0278412 A1 * | 12/2007 | Hackenschmied | G01T 1/2985 250/363.08 |
| 2007/0280410 A1 | 12/2007 | Lutz et al. | |
| 2011/0103021 A1 * | 5/2011 | Janssen | C08K 3/04 361/714 |
| 2012/0243661 A1 * | 9/2012 | Guo | A61B 6/035 378/19 |

FOREIGN PATENT DOCUMENTS

| | | | | |
|---|---|---|---|---|
| JP | 2004057834 A | | 2/2004 | |
| JP | 2011-516633 A | * | 5/2011 | ........... H01L 23/373 |

* cited by examiner

*Primary Examiner* — Glen Kao
(74) *Attorney, Agent, or Firm* — Fletcher Yoder, P.C.

(57) ABSTRACT

A radiation detecting apparatus is provided. The radiation detecting apparatus includes a plurality of detector modules arranged in a channel direction, each detector module including a plurality of detecting elements arranged in matrix form in the channel direction and a slice direction, and a heat radiating unit thermally coupled to the detecting elements and provided on an X-ray outgoing side of the detecting elements, a wind blowing unit configured to send wind to the heat radiating units of the detector modules in the slice direction, first wind shielding portions provided on a radiation outgoing side of the heat radiating units and configured to shield the wind in a radiation irradiating direction, and second wind shielding portions provided on a radiation incoming side of the heat radiating units and configured to shield the wind in the radiation irradiating direction.

18 Claims, 6 Drawing Sheets

RADIATION DETECTING APPARATUS AND RADIATION TOMOGRAPHIC IMAGING APPARATUS

CROSS REFERENCE TO RELATED APPLICATIONS

This application is a non-provisional application and claims priority to U.S. Provisional Patent Application Ser. No. 61/910,184 filed Nov. 29, 2013 for "RADIATION DETECTION APPARATUS AND RADIATION COMPUTED TOMOGRAPHY", which is hereby incorporated by reference in its entirety.

BACKGROUND

The present invention relates to a technology which stabilizes radiation detection characteristics of a radiation tomographic imaging apparatus.

It has been known that the radiation detection characteristics of a radiation tomographic imaging apparatus depend on the temperature of a detecting element in a radiation detecting apparatus therefor, particularly a photoelectric conversion element. On the other hand, the temperature of the detecting element has a strong tendency to gradually increase due to the generation of heat of electrical/electronic components disposed around the detecting element. Therefore, generally, a cooling system is provided in the radiation detecting apparatus to cool heating components or the like and control the temperature of a detecting element to be kept constant as much as possible, thereby achieving stabilization of the radiation detection characteristics.

As the cooling system mentioned above, an air cooling system using a cooling fan has been known. That is, wind is generated by the cooling fan, and the wind is applied to a substrate provided with detecting elements and a radiator disposed on the substrate, etc. to perform cooling. This system has heretofore been used because it is simple in structure and relatively easy to construct (refer to, for example, a Japanese Patent Laid-Open No. 2004-57834).

However, the generation of heat of the electrical/electronic components is often done in the vicinity of the detecting elements. Therefore, the heat is liable to be conducted to the detecting elements, and the control on the temperature of each detecting element often won't go as hoped in the cooling system.

The direction and volume of wind entering inside from the outside of the radiation detecting apparatus depend greatly on the rotational speed of a gantry rotating section equipped with the radiation detecting apparatus. Therefore, when the rotational speed of the gantry rotating section is changed, the temperature of the detecting element is also liable to change. That is, the cooling method using the cooling fan is not capable of sufficiently suppressing the change in the temperature of the detecting element and is difficult to achieve the stabilization of the detection characteristics.

With the foregoing situation in view, there has been a demand for a technology capable of when each detecting element of the radiation detecting apparatus in the radiation tomographic imaging apparatus is cooled, suppressing a change in the temperature of the detecting element and stabilizing detection characteristics.

BRIEF DESCRIPTION

According to the aspects described herein, since a first wind shielding unit is provided, it is possible to shield wind flowing from the outside of an X-ray detecting device upon rotation of a gantry rotating section. Since a second wind shielding unit is also provided, the blown wind is not applied directly to the detecting element side and can be applied to the heat radiating unit. As a result, the air cooling of each detecting element can be conducted more as designed and efficiently. It is possible to suppress a change in the temperature of the detecting element and achieve stabilization of radiation detection characteristics.

Further advantages will be apparent from the following description of the exemplary embodiments as illustrated in the accompanying drawings.

DETAILED DESCRIPTION

An exemplary embodiment will hereinafter be described. Incidentally, the disclosure is not limited to or by the exemplary embodiment.

Figure 1:
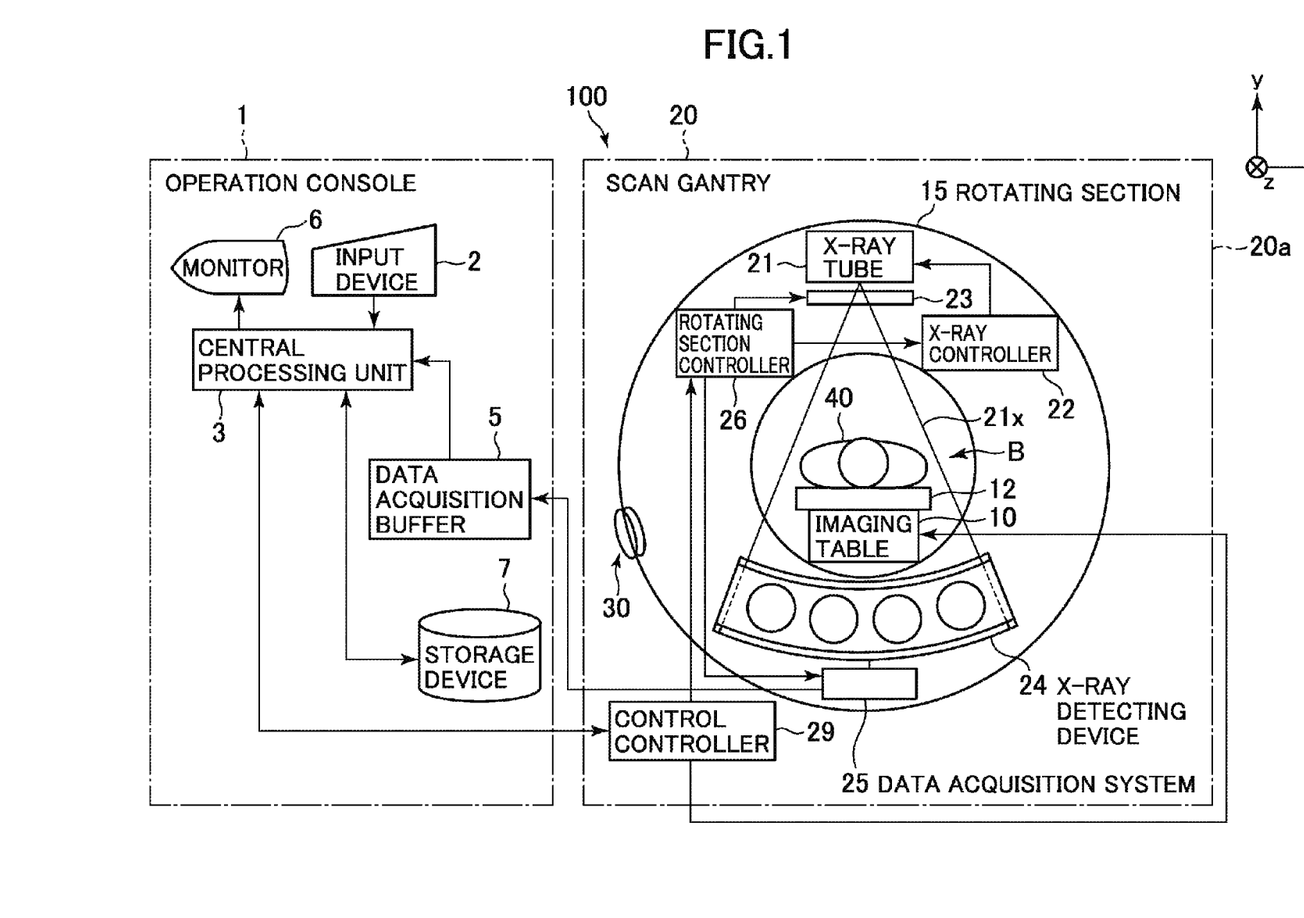
FIG. 1 is a diagram schematically showing a configuration of an X-ray CT apparatus.

FIG. 1 is a diagram schematically showing a configuration of an X-ray CT (Computed Tomography) apparatus according to the exemplary embodiment. As shown in FIG. 1, the X-ray CT apparatus 100 is equipped with an operation console 1, an imaging table 10 and a scan gantry 20.

The operation console 1 is equipped with an input device 2 which accepts an input from an operator, a central processing unit 3 which performs control of respective parts for performing imaging of a subject 40 to be imaged, a data process for generating an image, etc., a data acquisition buffer 5 which acquires data acquired by the scan gantry 20, a monitor 6 which displays an image thereon, and a storage device 7 which stores a program, data, etc. therein.

The imaging table 10 is equipped with a cradle 12 which inserts and draws the subject 40 into and from an opening B of the scan gantry 20 with the subject 40 placed thereon. The cradle 12 is elevated and linearly moved horizontally by a motor built in the imaging table 10. Incidentally, in the exemplary embodiment, the direction of a body axis of the subject 40, i.e., the horizontal linear moving direction of the cradle 12 is assumed to be a z direction, its vertical direction is assumed to be a y direction, and its horizontal direction orthogonal to the z and y directions is assumed to be an x direction.

The scan gantry 20 has an annular ring-shaped rotating section 15 which is rotatably supported about the opening B. The rotating section 15 is provided with an X-ray tube 21, an X-ray controller 22 which controls the X-ray tube 21, an aperture 23 which shapes X-rays 81 generated from the X-ray tube 21 into a fan beam or a cone beam, an X-ray detecting device 24 which detects the X-rays 81 penetrated through the subject 40, a DAS (Data Acquisition System) 25 which converts the outputs of the X-ray detecting device 24 into X-ray projection data and acquires the same, and a rotating section controller 26 which controls the X-ray controller 22, aperture 23, X-ray detecting device 24 and DAS 25. The scan gantry 20 is equipped with a control controller 29 which performs communication of control signals or the like with the operation console 1 and the imaging table 10. The rotating section 15 is electrically connected to a portion supporting it via a slip ring 30.

The X-ray tube 21 and the X-ray detecting device 24 are disposed opposite to each other with an imaging space in which the subject 40 is placed, i.e., the opening B of the scan gantry 20 interposed therebetween. When the rotating section 15 is rotated, the X-ray tube 21 and the X-ray detecting device 24 are rotated about the subject 40 while their positional relation is being maintained. The X-ray 21x of the fan beam or cone beam, which is radiated from the X-ray tube 21 and shaped by the aperture 23, penetrates the subject 40 and is applied onto the detection surface of the X-ray detecting device 24. The fan-angle direction of the fan beam or cone beam, i.e., the direction of expansion of the X-ray 21x at an xy plane is called a channel direction (CH direction), and the direction of expansion thereof in the z direction or the z direction itself is called a slice direction (SL direction). The direction in which the X-ray 21x is radiated from the X-ray tube 21 is called an X-ray irradiating direction (I direction).

The configuration of the X-ray detecting device 24 will now be described in detail.

Figure 2A:
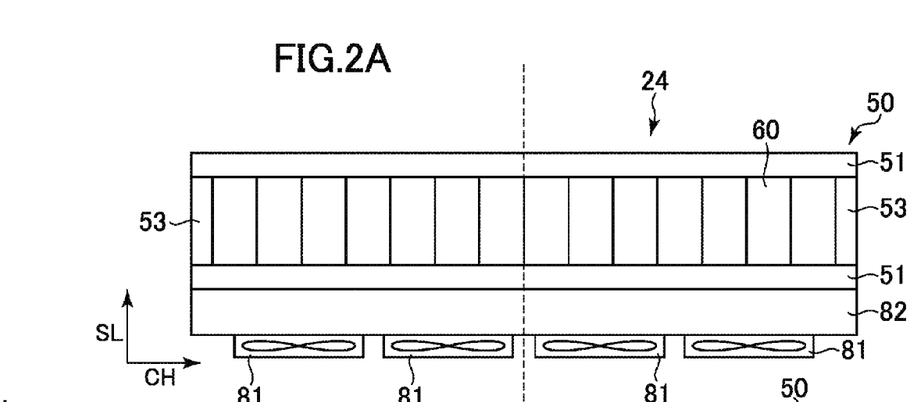
FIGS. 2A-2C are diagrams illustrating a configuration of an X-ray detecting apparatus.
Figure 2B:
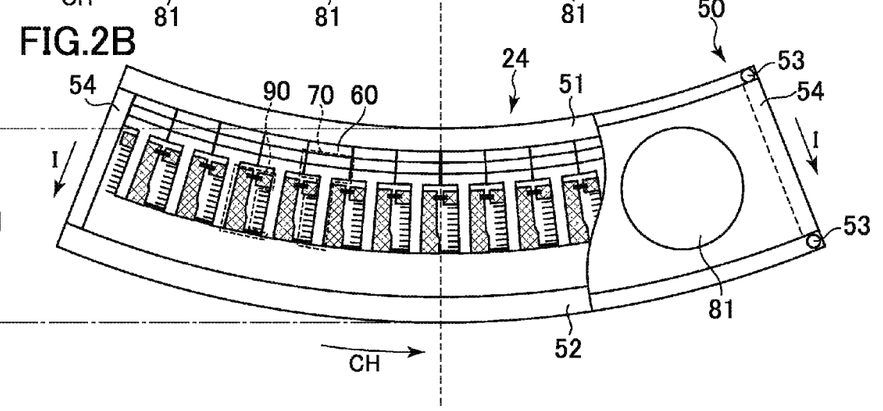
Figure 2C:
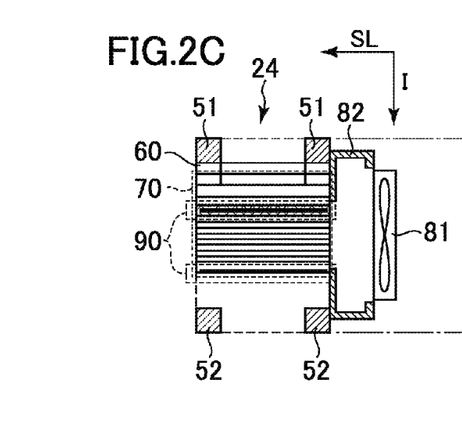

FIGS. 2A-2C are diagrams showing the configuration of the X-ray detecting device 24. FIGS. 2A and 2B are respectively diagrams as the X-ray detecting device 24 is seen in the I and SL directions and drawn as seen partly therethrough to make the configuration easy to understand. FIG. 2C is a diagram as the X-ray detecting device 24 is viewed in the CH direction and a sectional diagram in which a plane including the I and SL directions is taken as a section.

The X-ray detecting device 24 has a base frame 50, a plurality of collimator modules 60, and a plurality of detector modules 70.

The base frame 50 has a pair of X-ray incoming side rails 51, a pair of X-ray outgoing side rails 52, four first connecting members 53, and four second connecting members 54. The X-ray incoming side rails 51 respectively curvedly extend in an arc shape along the CH direction and are disposed to be parallel to each other at a predetermined interval as viewed in the SL direction. The X-ray outgoing side rails 52 respectively curvedly extend in an arc shape along the CH direction and are disposed to be parallel to each other at a predetermined interval as viewed in the SL direction. The X-ray outgoing side rails 52 are disposed to be approximately parallel to the X-ray incoming side rails 51 and the I direction. The four first connecting members 53 respectively extend in the SL direction and are disposed to connect the respective ends of the X-ray incoming side rails 51 and the respective ends of the X-ray outgoing side rails 52 to one another. Further, the four second connecting members 54 respectively extend in the I direction and are disposed to connect the respective ends of the X-ray incoming side rails 51 and the respective ends of the X-ray outgoing side rails 52 to one another.

The collimator modules 60 are respectively disposed on the X-ray outgoing side of the X-ray incoming side rails 51 in the base frame 50. The collimator modules 60 are arranged adjacent to each other along the CH direction. The collimator modules 60 are disposed thirty two, for example. The collimator modules 60 are respectively attached to the X-ray incoming side rails 51 of the base frame 50 by screw tightening. The collimator modules 60 respectively have a plurality of collimator plates (not shown) provided to divide detecting elements to be described later at least in the CH direction.

The detector modules 70 are disposed on the X-ray outgoing side of the collimator modules 60. The detector modules 70 are arranged adjacent to each other along the CH direction. The detector modules 70 are provided thirty two, for example. The detector modules 70 are aligned to positionally correspond to the collimator modules 60 in the CH direction. The detector modules 70 are respectively attached to the X-ray incoming side rails 51 of the base frame 50 by screw tightening.

The X-ray detecting device 24 also has a plurality of cooling fans 81 and a duct 82. The duct 82 is provided on the virtual end surface side of the base frame 50 as viewed in the SL direction. The cooling fans 81 are provided on the slice surface side of the duct 82. The cooling fans 81 generate wind by rotation thereof. This wind passes through the duct 82 and is substantially uniformly set out to the detector modules 70. Incidentally, the duct 82 is one example illustrative of a guide path.

The X-ray detecting device 24 further has wind flow adjustment component groups 90 for adjusting the flow of wind around the detector modules 70.

The configuration of the detector module 70 and the wind flow adjustment component group 90 will now be explained in detail.

The configuration of the detector module 70 will first be described.

Figure 3:
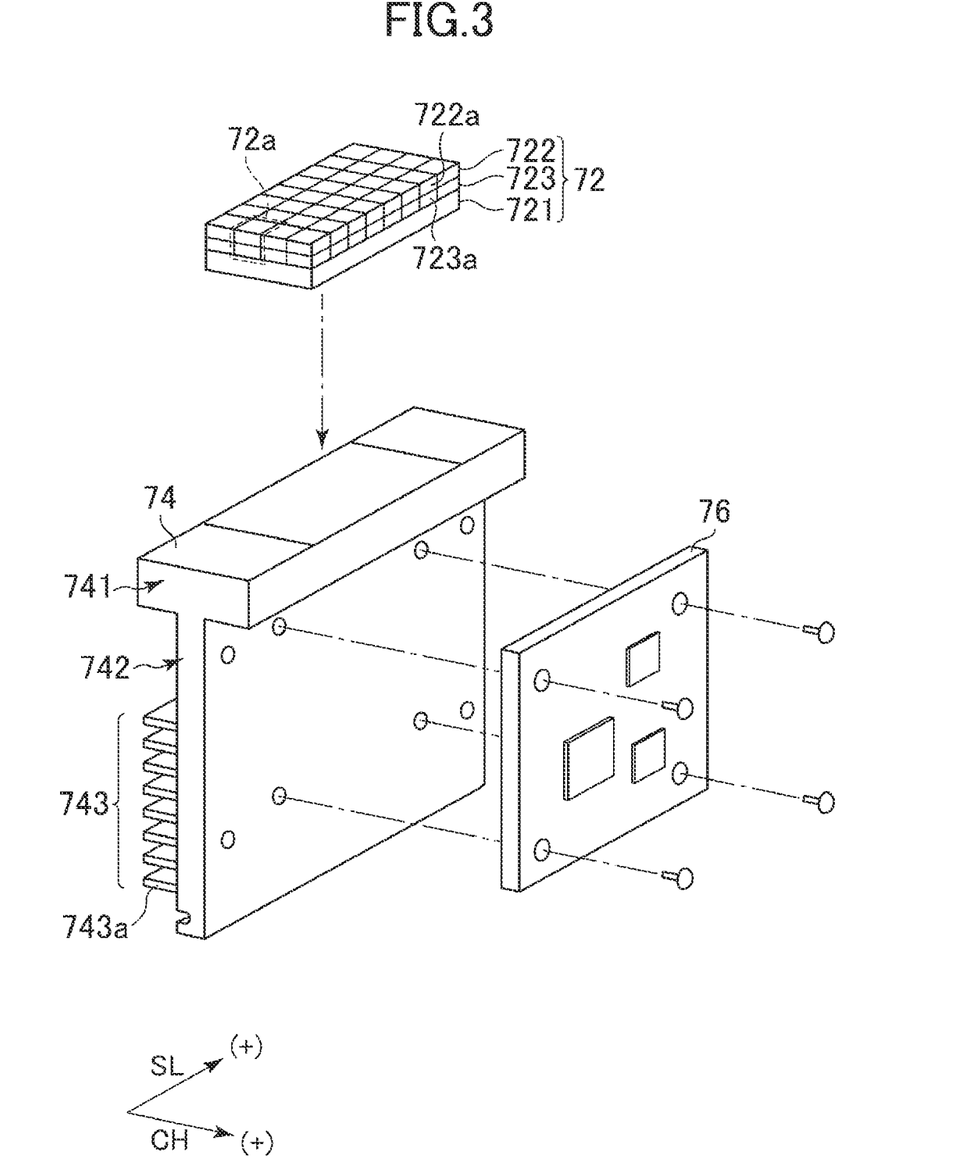
FIG. 3 is a diagram depicting a configuration of a detector module.
Figure 4:
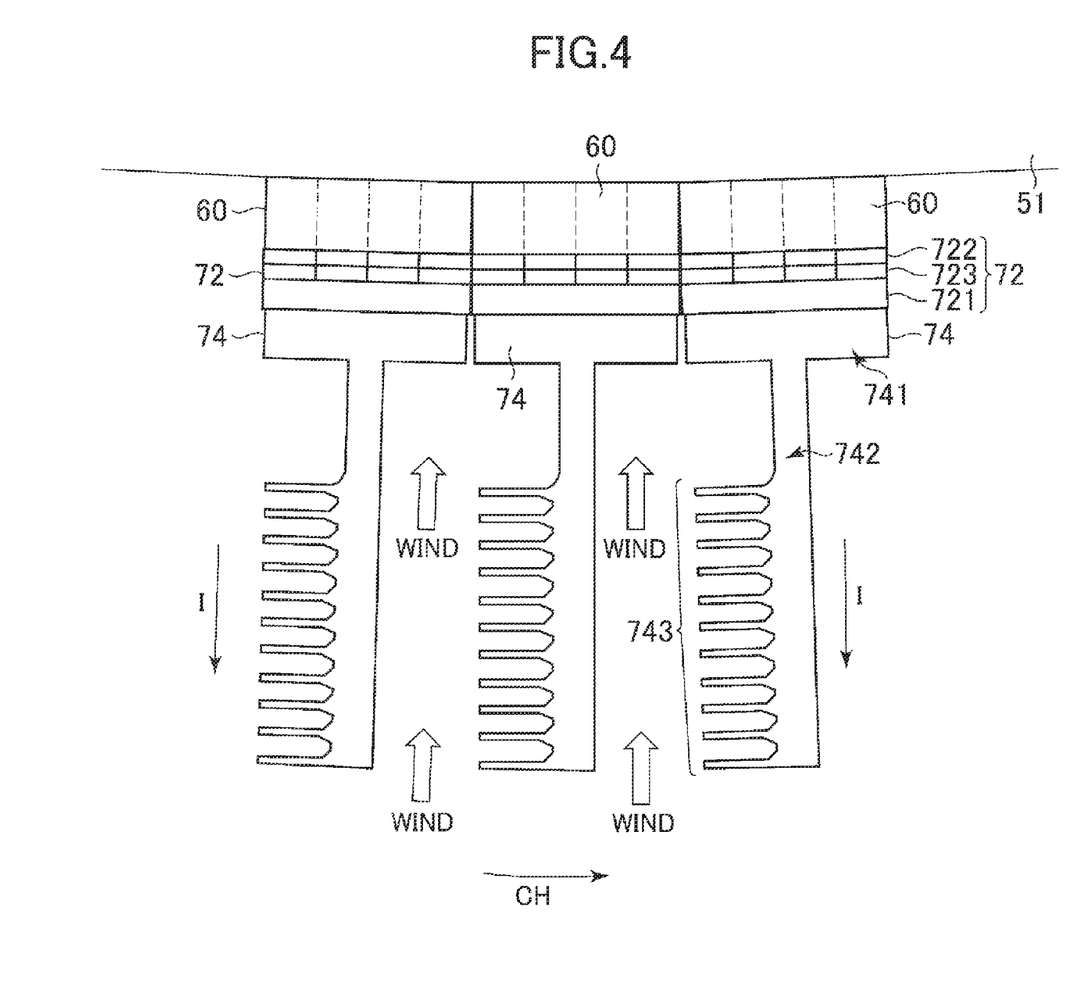
FIG. 4 is an enlarged diagram of a plurality of detector modules arranged in a channel direction.

FIG. 3 is a diagram showing the configuration of the detector module 70. FIG. 4 is an enlarged diagram of a plurality of detector modules 70 arranged in the channel direction (CH direction).

As shown in FIG. 3, the detector module 70 has a detecting element array block 72, a T-frame 74 and an electronic circuit block 76.

The detecting element array block 72 is comprised principally of a detecting element array substrate 721, a scintillator array 722 and a diode array 723.

The detecting element array substrate 721 has a plate shape close to a rectangular parallelepiped. The detecting element array substrate 721 is disposed in such a posture that the end sides thereof orthogonal to each other become parallel to the CH, SL and I directions respectively. The detecting element array substrate 721 has a wide plate surface on the X-ray incoming side. The detecting element array substrate 721 is comprised of ceramic or the like, for example.

The scintillator array 722 and the diode array 723 are provided on the plate surface on the X-ray incoming side of the detecting element array substrate 721 by laminating them in the I direction.

The scintillator array 722 has a plurality of scintillator elements 722a arranged in matrix form in the CH and SL directions. The scintillator element 722a converts incident X-rays into light. For example, 64 (CH direction)×128 (SL direction) scintillator elements 722a are arranged per detector module as the scintillator elements 722a.

The diode array 723 has a plurality of photo diode elements 723a arranged in matrix form in the CH and SL directions. The photo diode element 723a converts incident light into an electrical signal. For example, 64 (CH direction)×128 (SL direction) photo diode elements 723a are arranged per detector module as the photo diode elements 723a.

The scintillator elements 722a and the photo diode elements 723a positionally correspond to each other in the I direction. The scintillator element 722a and the photo diode element 723a constitute one detecting element 72a. That is, the X-rays incident on the detecting element 72a are converted into light by the scintillator element 722a, which in turn is converted into an electrical signal by the photo diode element 723a.

The T-frame 74 is a frame having a shape close to an alphabet T as seen in the SL direction. The T-frame 74 is made of an aluminum alloy or the like, for example. The T-frame 74 has a base portion 741, a columnar plate portion 742 and a fin unit 743.

The base portion 741 has a plate shape close to a rectangular parallelepiped. The base portion 741 is disposed in such a posture that their end sides orthogonal to each other respectively become parallel to the CH, SL and I directions. The base portion 741 has a plate surface wide on the X-ray incoming side.

The columnar plate portion 742 is arranged on the surface on the X-ray outgoing side of the base portion 741 and connected thereto. The columnar plate portion 742 has a plate shape close to a rectangular parallelepiped. The columnar plate portion 742 is disposed in such a posture that their end sides orthogonal to each other respectively become parallel to the CH, SL and I directions. The columnar plate portion 742 has substantially the same length as that of the base portion 741 as viewed in the SL direction. The columnar plate portion 742 has plate surfaces wide on both sides in the CH direction.

Incidentally, a first concave portion 742a which takes a concavity on the CH-direction+(plus) side and columnarly extends in the SL direction, is formed in the vicinity of the end on the X-ray outgoing side of the columnar plate portion 742 as shown in FIG. 3.

The fin unit 743 is arranged on the plate surface on the CH-direction plus side of the columnar plate portion and connected thereto. The fin unit 743 is comprised of a plurality of heat radiating plates 743a. The heat radiating plates 743a respectively have a plate shape close to the rectangular parallelepiped. The heat radiating plates 743a are respectively disposed in such a posture that their end sides orthogonal to each other respectively become parallel to the CH, SL and I directions. The heat radiating plates 743a respectively have substantially the same length as that of the base portion 741 in the SL direction. The heat radiating plates 743a respectively have plate surfaces wide on both sides in the I direction. The heat radiating plates 743a are provided at intervals nearly constant in the I direction.

Incidentally, in the exemplary embodiment, the base portion 741, the columnar plate portion 742 and the fin unit 743 are integrally formed.

The detecting element array substrate 721 is disposed on the plate surface on the X-ray incoming side of the base portion 741 in the T-frame 74 and fixed to the base portion 741 by screw tightening in close contact therewith.

The electronic circuit block 76 is arranged on the plate surface (plate surface on the side free of the fin unit 743) on one side in the CH direction of the columnar plate portion 742 of the T-frame 74 and fixed to the columnar plate portion 742 by screw tightening. The electronic circuit block 76 is connected to the detecting element array block 72 via a cable (not shown). Further, the electronic circuit block 76 is connected to the data acquisition system 25 via a cable (not shown). The electronic circuit block 76 includes an electronic circuit for processing a detection signal outputted from each detecting element 72a. The electronic circuit block 76 processes detection signals obtained from the detecting element array block 72 by the electronic circuit and sends the processed signals to the data acquisition system 25. The electronic circuit block 76 generates heat by energization.

As shown in FIG. 4, in the detector module 70 configured as described above, the electronic circuit block 76, the detecting element array block 72 and the T-frame 74 are thermally coupled to one another, and the T-frame 74 serves as a buffer to take a thermally balanced state. It is therefore possible to suppress sudden changes in temperature at the locations such as the electronic circuit block 76, the detecting element array block 72 and the like. Since the T-frame 74 is cooled by allowing wind sent from each cooling fan 81 through the duct 82 to blow against the fin unit 743, it is possible to suppress the entire temperature rise in the electronic circuit block 76, the detecting element array block 72 and the T-frame 74.

However, in the configuration brought by this, as shown in FIG. 4, it is not possible to prevent the entry of wind from the outside of the X-ray detecting device 24 when the rotating section 15 of the scan gantry 20 is rotated. Further, it is difficult to predict the way of entry of the wind therein because it changes depending on the rotational speed of the rotating section 15. Therefore, the control temperature as designed becomes extremely difficult. There is also a case where some of the wind from each cooling fan 81 directly applies to the base portion 741 of the T-frame 74 and promotes a change in the temperature of the detecting element array block 72. Further, since the wind from each of the cooling fans 81 passes through a relatively wide space between the adjacent T-frames 74, it does not apply only to the fin unit 743, thus resulting in insufficient cooling efficiency. In the exemplary embodiment, the wind flow adjustment component group 90 is provided to improve this situation.

Thus, the configuration of the wind flow adjustment component group 90 will be described.

Figure 5:
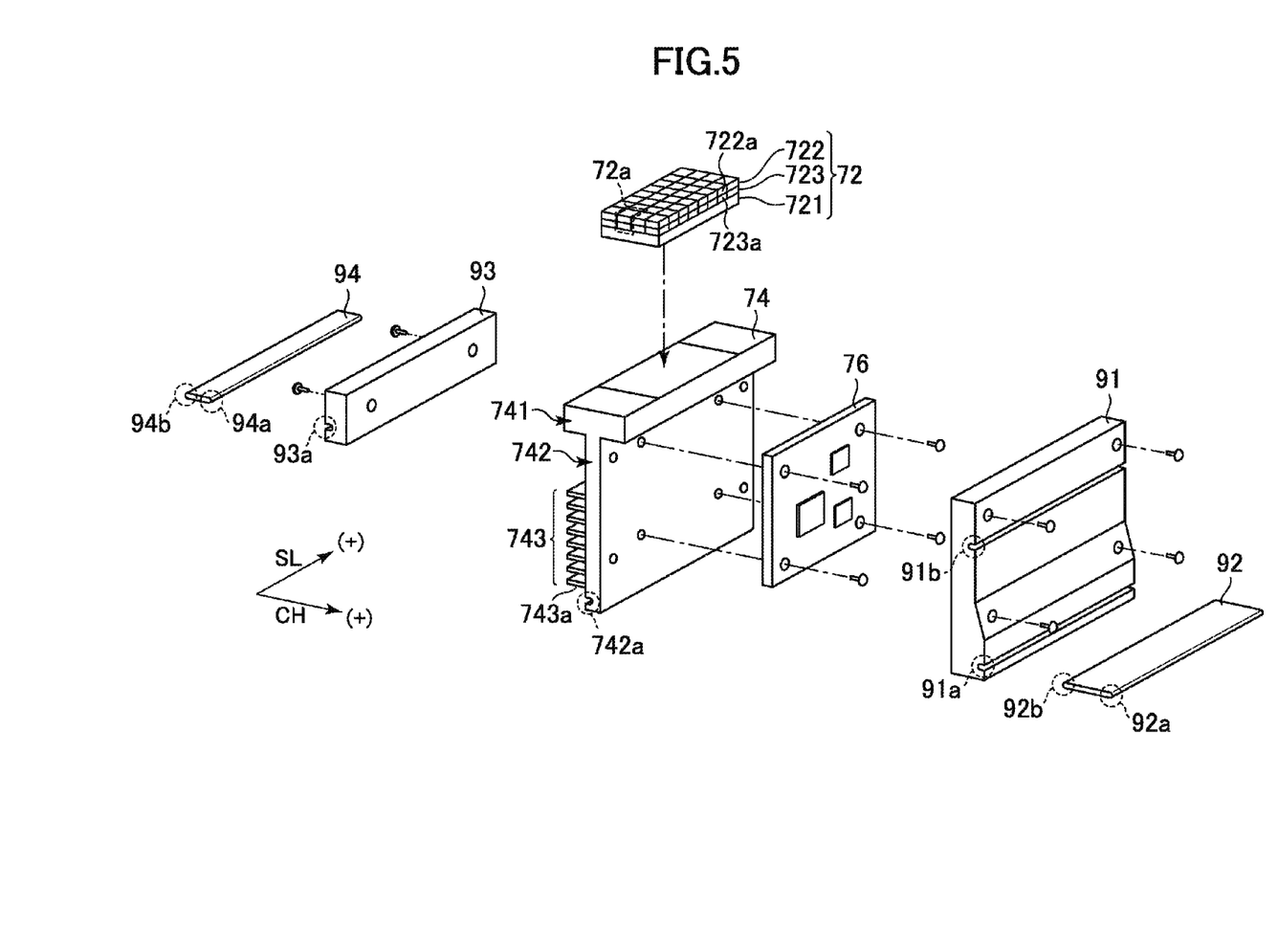
FIG. 5 is a diagram showing a configuration of a detector module and a wind flow adjustment component group.
Figure 6:
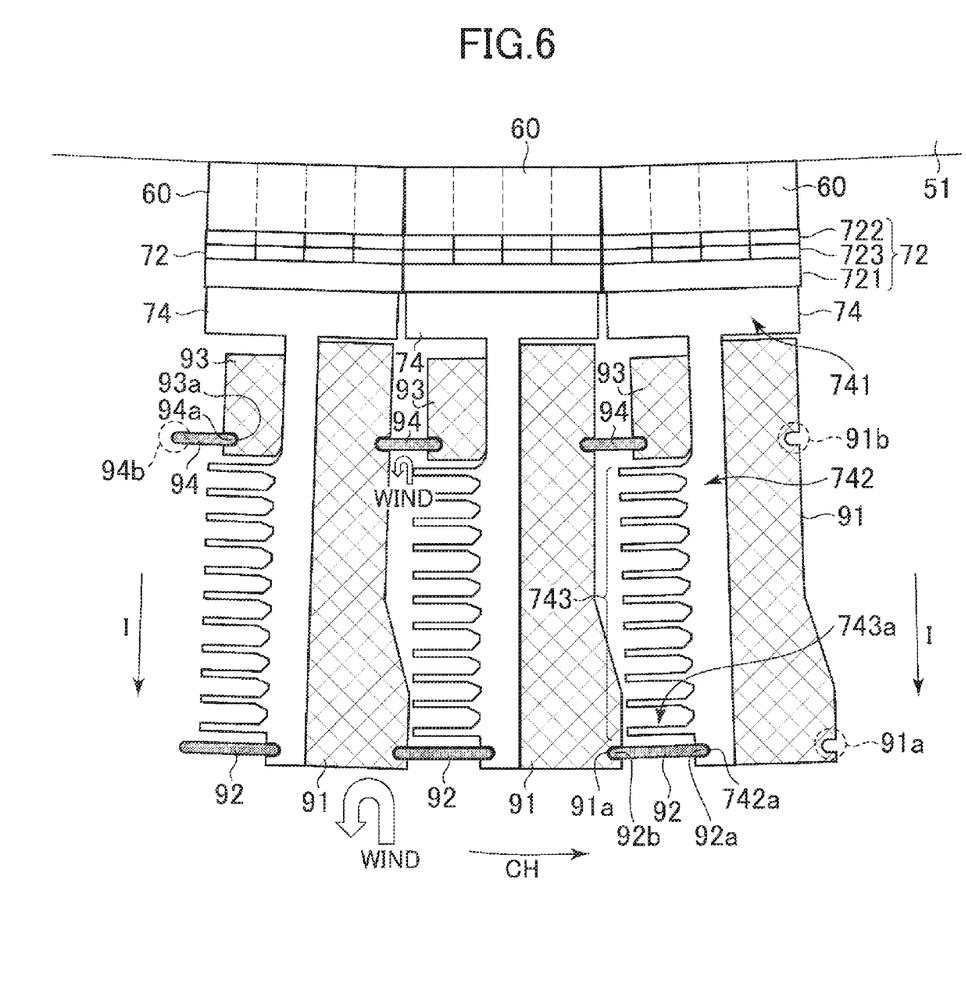
FIG. 6 is an enlarged diagram of a plurality of detector modules arranged in a channel direction and wind flow adjustment component groups attached thereto.

FIG. 5 is a diagram showing the configuration of the detector module 70 and the wind flow adjustment component group 90. FIG. 6 is an enlarged diagram of a plurality of detector modules 70 arranged in a channel direction (CH direction) and wind flow adjustment component groups 90 attached thereto.

As shown in FIGS. 5 and 6, the wind flow adjustment component group 90 includes a first cover portion 91, a first wind shielding plate 92, a second cover portion 93 and a second wind shielding plate 94. Incidentally, the first cover portion 91 and the first wind shielding plate 92 are one example illustrative of a first wind shielding unit. The second cover portion 93 and the second wind shielding plate 94 are one example illustrative of a second wind shielding unit. The first cover portion 91 is one example illustrative of a third wind shielding unit. The first wind shielding plate 92 is one example illustrative of a first plate member. Further, the second wind shielding plate 94 is one example illustrative of a second plate member.

Any of the first cover portion 91, the first wind shielding plate 92, the second cover portion 93 and the second wind shielding plate 94 is comprised of conductive plastic. The conductive plastic may be substantial conductive plastic or composite conductive plastic. The substantial conductive plastic is plastic having conductivity derived from the original polymer structure. Polyacetylene, polypyrrole, polythiophene and polyaniline, etc. are considered as the substantial conductive plastic. The composite conductive plastic is plastic given conductivity by kneading an inorganic conductor such as a metal, carbon fiber or the like into non-conductive plastic or forming a conductor thin film in the surface of the non-conductive plastic.

The first cover portion 91 has a substantially box shape capable of containing the electronic circuit block 76 therein. The first cover portion 91 has substantially the same length as that of the base portion 741 in the SL direction. The width in the CH direction of the first cover portion 91 is a width of about 60% to 90% of the width formed between the columnar plate portion 742 of the detector module 70 and the fin unit 743 of the detector module 70 disposed adjacent thereto. The first cover portion 91 is disposed on the plate surface on the CH-direction minus side of the columnar plate portion 742 of the T-frame 74 so as to cover the electronic circuit block 76 and fixed to the columnar plate portion 742 by screw tightening.

A second concave portion 91a which takes a concavity on the CH-direction—(minus) side and columnarly extends in the SL direction, is formed in a portion located on the surface on the CH-direction plus side of the first cover portion 91 and closer to the X-ray outgoing side (+I direction) than the fin unit 743 as viewed in the I direction. A third concave portion 91b which takes a concavity on the CH-direction minus side and columnarly extends in the SL direction, is formed in a portion located on the surface on the CH-direction plus side of the first cover portion 91 and closer to the X-ray incoming side (−I direction) than the fin unit 743 as viewed in the I direction.

The second cover portion 93 is disposed in a region on the plate surface on the CH-direction minus side of the columnar plate portion 742 of the T-frame 74 and located on the X-ray incoming side than the fin unit 743 and is fixed to the columnar plate portion 742 by screw tightening. A fourth concave portion 93a which assumes a concavity on the CH-direction plus side and columnarly extends in the SL direction, is formed in a portion on the CH-direction minus side of the second cover portion 93.

The first wind shielding plate 92 has a plate shape close to the rectangular parallelepiped. The plate surface of the first wind shielding plate 92 is rectangular, and the two end sides of the plate surface orthogonal to each other are approximately parallel to the CH and SL directions respectively. Thus, the thickness direction of the first wind shielding plate 92 is substantially parallel to the I direction. The first wind shielding plate 92 has approximately the same width as that between the first cover portion 91 and the second cover portion 93 adjacent to each other in the CH direction and has approximately the same length as that of the base portion 741 in the SL direction. A first convex portion 92a and a second convex portion 92b each of which assumes a convexity in the CH direction are formed at both ends in the CH direction of the first wind shielding plate 92. These first and second convex portions 92a and 92b are respectively formed in such a shape as to engage with the first and second concave portions 742a and 91a. The first wind shielding plate 92 is inserted in the SL direction in a state in which the first and second convex portions 92a and 92b are engaged with the first and second convex portions 742a and 91a respectively, and fixed by friction of their engagement parts.

The second wind shielding plate 94 has a plate shape close to the rectangular parallelepiped. The plate surface of the second wind shielding plate 94 is rectangular, and the two end sides of the plate surface orthogonal to each other are approximately parallel to the CH and SL directions respectively. Thus, the thickness direction of the second wind shielding plate 94 is substantially parallel to the I direction. The second wind shielding plate 94 has approximately the same width as that between the first cover portion 91 and the columnar plate portion 742 of the T-frame 74 adjacent to each other in the CH direction and has approximately the same length as that of the base portion 741 in the SL direction. A third convex portion 94a and a fourth convex portion 94b each of which assumes a convexity in the CH direction are formed at both ends in the CH direction of the second wind shielding plate 94. The third convex portion 94a and the fourth convex portion 94b are respectively formed in such a shape as to engage with the first and second concave portions 91b and 93a. The second wind shielding plate 94 is inserted in the SL direction in a state in which the third convex portion 94a and the fourth convex portion 94b are respectively engaged with the first and second concave portions 91b and 93a, and is fixed by friction of their engagement parts.

According to the exemplary embodiment such as described above, since the first cover portion 91 and the first wind shielding plate 92 mentioned above are provided, it is possible to shield wind flowing inside from the outside of the X-ray detecting device 24 upon rotation of the rotating section 15 of the scan gantry 20. Since the second cover portion 93 and the second wind shielding plate 94 mentioned above are provided, the wind sent from each of the cooling fans 81 can be applied to the fin unit 743 of the T-frame 74 without being applied directly to the base portion 741 of the T-frame 74 to which the detecting element array block 72 provided with the detecting elements 72a is connected. As a result, cooling by the wind blowing from the cooling fan 81 can be conducted as designed and efficiently. It is possible to suppress a change in the temperature of the detecting element 72a and achieve stabilization of radiation detection characteristics.

According to the exemplary embodiment as well, since the second cover portion 93 and the second wind shielding plate 94 are provided, it is possible to shield the entry of unintentional light into the detecting element 72a and suppress a light leak, i.e., a misdetection of light.

Further, according to the exemplary embodiment, since there is provided the first cover portion 91 mentioned above, the wind blowing from each cooling fan 81 can be applied substantially to only the fin unit 743 of the T-frame 74 without leaking outside. As a result, cooling efficiency can be further improved. It is also possible to further shield light entering from the outside and further suppress a light leak.

Furthermore, according to the exemplary embodiment, since the first cover 91 and the first wind shielding plate 92, and the second cover portion 93 and the second wind shielding plate 94 are made of plastic, they are light in weight. They are capable of suppressing the generation of distortion due to the large mass of the X-ray detecting device 24 upon the rotation of the scan gantry 20, thus improving X-ray detection accuracy.

Still further, according to the exemplary embodiment, since the first cover portion 91 and the first wind shielding plate 92, and the second cover portion 93 and the second wind shielding plate 94 have conductivity, it is possible to shield external electromagnetic wave noise and enhance the accuracy of a detection signal.

Still further, according to the exemplary embodiment, the first cover portion 91 is formed between the fin units 743 so as to have a width of about 60% to 90% of the width formed between the columnar plate portion 742 of the detector module 70 and the fin unit 743 of the detector module 70 disposed adjacent thereto. Since the constant width is ensured in this manner, it is possible to reduce the friction of air blowing from each cooling fan 81 against the fin unit 743 and lighten the load of the cooling fan 81.

Since the first and second wind shielding plates 92 and 94 are fixed only by the friction without using screws or the like, assembly man-hours and cost can be reduced. The targeted detector module 70 can be separated from other detector modules 70 only by detaching the first and second wind shielding plates 92 and 94 attached to the detector module 70 targeted for maintenance. Maintainability is very good.

Incidentally, the disclosure is not limited to the exemplary embodiment and can be changed in various ways within the scope not departing from the spirit of the invention.

For example, in the exemplary embodiment, the second cover portion 93 and the second wind shielding plate 94 are combined together to prevent wind from directly applying to the base portion 741 of the T-frame 74, but the similar effect may be obtained using an integrally-formed wind shielding plate.

Further, for example, as to the engagement parts of the SL-direction both ends of the first and second wind shielding plates 92 and 94, any structure may be adopted if fixable by friction.

Furthermore, for example, the systems and methods described herein can be applied even to a PET-CT apparatus or SPECT-CT apparatus in which the X-ray CT apparatus and PET (Polyethylene Terephthalate) or SPECT (Single Photon Emission Computed Tomography) are combined together, etc.

What is claimed is:

1. A radiation detecting apparatus for a radiation tomographic imaging apparatus, comprising:
   a plurality of detector modules arranged in a channel direction, each detector module including a plurality of detecting elements arranged in matrix form in the channel direction and a slice direction, and a heat radiating unit thermally coupled to the detecting elements and provided on an X-ray outgoing side of the detecting elements;
   a wind blowing unit configured to send wind to the heat radiating units of the detector modules in the slice direction;
   first wind shielding portions provided on a radiation outgoing side of the heat radiating units and extending between the heat radiating units adjacent to each other in the channel direction, the first wind shielding portions configured to shield the wind in a radiation irradiating direction;
   second wind shielding portions provided on a radiation incoming side of the heat radiating units and extending between the heat radiating units adjacent to each other in the channel direction, the second wind shielding portions configured to shield the wind in the radiation irradiating direction;
   wherein each of the first wind shielding portions includes a first plate member which has a plate thickness extending substantially in the radiation irradiating direction and has engagement parts directly or indirectly engaged with the adjacent heat radiating units at both ends of the first wind shielding portion in the channel direction, and
   wherein the first plate member is fixed to the adjacent heat radiating units by the friction of the engagement parts.

2. The radiation detecting apparatus according to claim 1, wherein each of the second wind shielding portions includes a second plate member which has a plate thickness extending substantially in the radiation irradiating direction and has engagement parts directly or indirectly engaged with adjacent heat radiating units at both ends of the second wind shielding portion in the channel direction, and
   wherein the second plate member is fixed to the adjacent heat radiating units by the friction of the engagement parts.

3. The radiation detecting apparatus according to claim 1, wherein the first and second wind shielding portions are comprised of plastic.

4. The radiation detecting apparatus according to claim 3, wherein the plastic that constitutes the first and second wind shielding portions has conductivity.

5. The radiation detecting apparatus according to claim 1, further including third wind shielding portions configured to shield wind in the slice direction between the adjacent heat radiating units.

6. The radiation detecting apparatus according to claim 5, wherein each of the third wind shielding portions has a width of approximately 60% to 90% of the width between the adjacent heat radiating units in the channel direction.

7. The radiation detecting apparatus according to claim 5, wherein the third wind shielding portion is comprised of plastic.

8. The radiation detecting apparatus according to claim 7, wherein the plastic that constitutes the third wind shielding portion has conductivity.

9. The radiation detecting apparatus according to claim 1, wherein each of the detector modules have an electronic circuit unit configured to process a detection signal, and
   wherein the electronic circuit unit is thermally coupled to the heat radiating unit.

10. The radiation detecting apparatus according to claim 1, wherein each of the detecting elements include a first element configured to convert radiation into light, and a second element configured to convert the light into an electrical signal.

11. The radiation detecting apparatus according to claim 1, wherein the heat radiating unit includes a plurality of heat radiating plates provided at intervals in the radiation irradiating direction.

12. The radiation detecting apparatus according to claim 1, wherein the wind blowing unit includes cooling fans configured to generate wind, and a guide path configured to guide the wind to the heat radiating units.

13. A radiation tomographic imaging apparatus comprising:
   a radiation source; and
   a radiation detecting apparatus,
   wherein said radiation tomographic imaging apparatus is configured to radiate radiation while rotating the radiation source and the radiation detecting apparatus around an object to be imaged and perform tomography of the object, and
   wherein said radiation detecting apparatus comprises:
   a plurality of detector modules arranged in a channel direction, each detector module including a plurality of detecting elements arranged in matrix form in the channel direction and a slice direction, and a heat radiating unit thermally coupled to the detecting elements and provided on an X-ray outgoing side of the detecting elements;
   a wind blowing unit configured to send wind to the heat radiating units of the detector modules in the slice direction;

first wind shielding portions provided on a radiation outgoing side of the heat radiating units and extending between the heat radiating units adjacent to each other in the channel direction, the first wind shielding portions configured to shield the wind in a radiation irradiating direction; and second wind shielding portions provided on a radiation incoming side of the heat radiating units and extending between the heat radiating units adjacent to each other in the channel direction, the second wind shielding portions configured to shield the wind in the radiation irradiating direction;

wherein each of the first wind shielding portions includes a first plate member which has a plate thickness extending substantially in the radiation irradiating direction and has engagement parts directly or indirectly engaged with the adjacent heat radiating units at both ends of the first wind shielding portion in the channel direction, and wherein the first plate member is fixed to the adjacent heat radiating units by the friction of the engagement parts.

14. The radiation tomographic imaging apparatus according to claim 13, wherein each of the second wind shielding portions includes a second plate member which has a plate thickness extending substantially in the radiation irradiating direction and has engagement parts directly or indirectly engaged with adjacent heat radiating units at both ends of the second wind shielding portion in the channel direction, and wherein the second plate member is fixed to the adjacent heat radiating units by the friction of the engagement parts.

15. The radiation tomographic imaging apparatus according to claim 13, wherein the radiation detecting apparatus further includes third wind shielding portions configured to shield wind in the slice direction between the adjacent heat radiating units.

16. The radiation tomographic imaging apparatus according to claim 13, wherein each of the detector modules have an electronic circuit unit configured to process a detection signal, and wherein the electronic circuit unit is thermally coupled to the heat radiating unit.

17. The radiation tomographic imaging apparatus according to claim 13, wherein the heat radiating unit includes a plurality of heat radiating plates provided at intervals in the radiation irradiating direction.

18. The radiation tomographic imaging apparatus according to claim 13, wherein the wind blowing unit includes cooling fans configured to generate wind, and a guide path configured to guide the wind to the heat radiating units.

* * * * *